(12) United States Patent
Pacetti et al.

(10) Patent No.: US 8,062,353 B2
(45) Date of Patent: *Nov. 22, 2011

(54) ABLUMINAL, MULTILAYER COATING CONSTRUCTS FOR DRUG-DELIVERY STENTS

(75) Inventors: Stephen Dirk Pacetti, San Jose, CA (US); Jessica DesNoyer, San Jose, CA (US); Yung-Ming Chen, Cupertino, CA (US); Lothar Kleiner, Los Altos, CA (US); Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/617,593

(22) Filed: Nov. 12, 2009

(65) Prior Publication Data

US 2010/0057198 A1 Mar. 4, 2010

Related U.S. Application Data

(63) Continuation of application No. 11/015,313, filed on Dec. 16, 2004, now Pat. No. 7,632,307.

(51) Int. Cl.
*A61F 2/06* (2006.01)
(52) U.S. Cl. .................................... 623/1.44
(58) Field of Classification Search ........ 623/1.15–1.16, 623/1.398–1.54, 1.38–1.46
See application file for complete search history.

(56) References Cited

U.S. PATENT DOCUMENTS

| | | | | | |
|---|---|---|---|---|---|
| 5,081,394 | A | * | 1/1992 | Morishita et al. | 313/466 |
| 5,084,065 | A | * | 1/1992 | Weldon et al. | 623/1.44 |
| 5,108,417 | A | * | 4/1992 | Sawyer | 623/1.22 |
| 5,108,755 | A | * | 4/1992 | Daniels et al. | 424/426 |
| 5,112,457 | A | * | 5/1992 | Marchant | 204/165 |
| 5,123,917 | A | * | 6/1992 | Lee | 623/22.26 |
| 5,156,623 | A | * | 10/1992 | Hakamatsuka et al. | 604/890.1 |
| 5,290,271 | A | * | 3/1994 | Jernberg | 604/891.1 |
| 5,306,286 | A | * | 4/1994 | Stack et al. | 623/1.12 |
| 5,342,283 | A | * | 8/1994 | Good | 600/8 |
| 5,423,885 | A | * | 6/1995 | Williams | 623/1.17 |
| 5,441,515 | A | * | 8/1995 | Khosravi et al. | 606/194 |
| 5,500,013 | A | * | 3/1996 | Buscemi et al. | 623/1.22 |
| 5,551,954 | A | * | 9/1996 | Buscemi et al. | 623/1.15 |
| 5,556,413 | A | * | 9/1996 | Lam | 623/1.2 |
| 5,578,046 | A | * | 11/1996 | Liu et al. | 606/151 |

(Continued)

FOREIGN PATENT DOCUMENTS

EP 0 950 386 10/1999

(Continued)

OTHER PUBLICATIONS

European Patent Opposition for EP 1827308, mailed Sep. 14, 2010, 5 pgs.

(Continued)

*Primary Examiner* — Alvin J Stewart
(74) *Attorney, Agent, or Firm* — Squire, Sanders & Dempsey (US) LLP

(57) ABSTRACT

Implantable medical devices may include at least one structural element having an abluminal side, luminal side, and sidewalls between the abluminal and luminal sides. The coating may include at least two continuous coating layers. In some embodiments, the luminal side, and all or a majority of the sidewalls are free of at least two of the coating layers.

21 Claims, 8 Drawing Sheets

U.S. PATENT DOCUMENTS

| | | | |
|---|---|---|---|
| 5,578,073 A * | 11/1996 | Haimovich et al. | 623/1.48 |
| 5,618,299 A * | 4/1997 | Khosravi et al. | 623/1.2 |
| 5,629,077 A * | 5/1997 | Turnlund et al. | 623/1.15 |
| 5,674,242 A * | 10/1997 | Phan et al. | 606/198 |
| 5,693,085 A * | 12/1997 | Buirge et al. | 623/1.13 |
| 5,725,549 A * | 3/1998 | Lam | 623/1.15 |
| 5,788,979 A * | 8/1998 | Alt et al. | 424/426 |
| 5,800,392 A * | 9/1998 | Racchini | 604/103.01 |
| 5,824,056 A * | 10/1998 | Rosenberg | 623/66.1 |
| 5,830,217 A * | 11/1998 | Ryan | 623/1.11 |
| 5,833,651 A * | 11/1998 | Donovan et al. | 604/509 |
| 5,836,962 A * | 11/1998 | Gianotti | 623/1.51 |
| 5,871,436 A * | 2/1999 | Eury | 600/3 |
| 5,873,904 A * | 2/1999 | Ragheb et al. | 623/1.13 |
| 5,972,027 A * | 10/1999 | Johnson | 623/1.42 |
| 6,010,445 A * | 1/2000 | Armini et al. | 600/3 |
| 6,010,530 A * | 1/2000 | Goicoechea | 623/1.13 |
| 6,027,526 A * | 2/2000 | Limon et al. | 623/1.15 |
| 6,066,156 A * | 5/2000 | Yan | 606/192 |
| 6,071,305 A * | 6/2000 | Brown et al. | 623/1.43 |
| 6,080,190 A * | 6/2000 | Schwartz | 623/1.22 |
| 6,086,610 A * | 7/2000 | Duerig et al. | 623/1.18 |
| 6,099,561 A * | 8/2000 | Alt | 623/1.44 |
| 6,099,562 A * | 8/2000 | Ding et al. | 623/1.46 |
| 6,103,230 A * | 8/2000 | Billiar et al. | 424/94.4 |
| 6,106,454 A * | 8/2000 | Berg et al. | 600/3 |
| 6,106,530 A * | 8/2000 | Harada | 623/1.11 |
| 6,107,416 A * | 8/2000 | Patnaik et al. | 525/453 |
| 6,120,535 A * | 9/2000 | McDonald et al. | 623/1.39 |
| 6,120,847 A * | 9/2000 | Yang et al. | 427/335 |
| 6,139,573 A * | 10/2000 | Sogard et al. | 623/1.15 |
| 6,153,252 A * | 11/2000 | Hossainy et al. | 427/2.3 |
| 6,165,212 A * | 12/2000 | Dereume et al. | 623/1.13 |
| 6,224,626 B1 * | 5/2001 | Steinke | 623/1.16 |
| 6,248,344 B1 * | 6/2001 | Ylanen et al. | 424/423 |
| 6,251,136 B1 * | 6/2001 | Guruwaiya et al. | 623/1.46 |
| 6,253,443 B1 * | 7/2001 | Johnson | 29/557 |
| 6,254,632 B1 * | 7/2001 | Wu et al. | 623/1.15 |
| 6,258,099 B1 * | 7/2001 | Mareiro et al. | 606/108 |
| 6,258,121 B1 * | 7/2001 | Yang et al. | 623/1.46 |
| 6,273,913 B1 * | 8/2001 | Wright et al. | 623/1.42 |
| 6,287,628 B1 * | 9/2001 | Hossainy et al. | 427/2.3 |
| 6,290,721 B1 * | 9/2001 | Heath | 623/1.15 |
| 6,293,966 B1 * | 9/2001 | Frantzen | 623/1.15 |
| 6,312,459 B1 * | 11/2001 | Huang et al. | 623/1.15 |
| 6,364,903 B2 * | 4/2002 | Tseng et al. | 623/1.15 |
| 6,379,379 B1 * | 4/2002 | Wang | 623/1.15 |
| 6,379,381 B1 * | 4/2002 | Hossainy et al. | 623/1.42 |
| 6,387,121 B1 * | 5/2002 | Alt | 623/1.15 |
| 6,413,272 B1 * | 7/2002 | Igaki | 623/1.15 |
| 6,419,692 B1 * | 7/2002 | Yang et al. | 623/1.15 |
| 6,436,816 B1 * | 8/2002 | Lee et al. | 438/643 |
| 6,444,567 B1 * | 9/2002 | Besser et al. | 438/625 |
| 6,455,424 B1 * | 9/2002 | McTeer et al. | 438/675 |
| 6,462,284 B1 * | 10/2002 | Hashimoto | 174/260 |
| 6,468,906 B1 * | 10/2002 | Chan et al. | 438/687 |
| 6,485,512 B1 * | 11/2002 | Cheng | 623/1.21 |
| 6,488,701 B1 * | 12/2002 | Nolting et al. | 623/1.13 |
| 6,491,666 B1 * | 12/2002 | Santini et al. | 604/191 |
| 6,492,615 B1 * | 12/2002 | Flanagan | 219/121.66 |
| 6,494,908 B1 * | 12/2002 | Huxel et al. | 623/1.22 |
| 6,495,200 B1 * | 12/2002 | Chan et al. | 438/626 |
| 6,503,954 B1 | 1/2003 | Bhat et al. | |
| 6,506,437 B1 * | 1/2003 | Harish et al. | 427/2.25 |
| 6,517,888 B1 * | 2/2003 | Weber | 427/2.24 |
| 6,530,950 B1 * | 3/2003 | Alvarado et al. | 623/1.13 |
| 6,530,951 B1 * | 3/2003 | Bates et al. | 623/1.45 |
| 6,626,939 B1 * | 9/2003 | Burnside et al. | 623/1.38 |
| 6,645,243 B2 * | 11/2003 | Vallana et al. | 623/1.46 |
| 6,660,034 B1 * | 12/2003 | Mandrusov et al. | 623/1.42 |
| 6,663,662 B2 * | 12/2003 | Pacetti et al. | 623/1.13 |
| 6,664,187 B1 * | 12/2003 | Ngo et al. | 438/687 |
| 6,666,214 B2 * | 12/2003 | Canham | 128/899 |
| 6,673,105 B1 * | 1/2004 | Chen | 623/1.15 |
| 6,673,154 B1 * | 1/2004 | Pacetti et al. | 118/500 |
| 6,676,700 B1 * | 1/2004 | Jacobs et al. | 623/1.34 |
| 6,677,357 B2 | 1/2004 | Zhu et al. | |
| 6,702,850 B1 * | 3/2004 | Byun et al. | 623/1.44 |
| 6,716,444 B1 * | 4/2004 | Castro et al. | 424/422 |
| 6,719,934 B2 * | 4/2004 | Stinson | 264/40.1 |
| 6,752,826 B2 * | 6/2004 | Holloway et al. | 623/1.13 |
| 6,753,071 B1 * | 6/2004 | Pacetti | 428/212 |
| 6,758,859 B1 * | 7/2004 | Dang et al. | 623/1.15 |
| 6,764,505 B1 * | 7/2004 | Hossainy et al. | 623/1.15 |
| 6,774,278 B1 * | 8/2004 | Ragheb et al. | 623/1.1 |
| 6,849,089 B2 * | 2/2005 | Stoll | 623/1.42 |
| 6,981,985 B2 | 1/2006 | Brown et al. | |
| 2001/0044652 A1 * | 11/2001 | Moore | 623/1.16 |
| 2002/0032414 A1 * | 3/2002 | Ragheb et al. | 604/265 |
| 2002/0082679 A1 * | 6/2002 | Sirhan et al. | 623/1.15 |
| 2002/0082680 A1 * | 6/2002 | Shanley et al. | 623/1.16 |
| 2002/0116050 A1 * | 8/2002 | Kocur | 623/1.15 |
| 2002/0183581 A1 * | 12/2002 | Yoe et al. | 600/3 |
| 2003/0028243 A1 * | 2/2003 | Bates et al. | 623/1.15 |
| 2003/0028244 A1 * | 2/2003 | Bates et al. | 623/1.15 |
| 2003/0036794 A1 * | 2/2003 | Ragheb et al. | 623/1.15 |
| 2003/0054090 A1 * | 3/2003 | Hansen | 427/2.1 |
| 2003/0060877 A1 * | 3/2003 | Falotico et al. | 623/1.42 |
| 2003/0069631 A1 | 4/2003 | Stoll | |
| 2003/0073961 A1 * | 4/2003 | Happ | 604/274 |
| 2003/0077310 A1 | 4/2003 | Pathak et al. | |
| 2003/0088307 A1 * | 5/2003 | Shulze et al. | 623/1.15 |
| 2003/0100865 A1 * | 5/2003 | Santini et al. | 604/161 |
| 2003/0113439 A1 * | 6/2003 | Pacetti et al. | 427/2.24 |
| 2004/0047980 A1 * | 3/2004 | Pacetti et al. | 427/2.25 |
| 2004/0170685 A1 | 9/2004 | Carpenter | |
| 2004/0213893 A1 * | 10/2004 | Boulais | 427/2.24 |
| 2004/0236417 A1 * | 11/2004 | Yan et al. | 623/1.43 |
| 2005/0187607 A1 * | 8/2005 | Akhtar et al. | 623/1.15 |

FOREIGN PATENT DOCUMENTS

| | | |
|---|---|---|
| EP | 0 970711 | 1/2000 |
| WO | WO 95/06487 | 3/1995 |
| WO | WO 96/33672 | 10/1996 |
| WO | WO 01/91918 | 12/2001 |
| WO | WO 03/009779 | 2/2003 |
| WO | WO 03/090818 | 11/2003 |
| WO | WO 03/099169 | 12/2003 |

OTHER PUBLICATIONS

International Search Report for PCT/US2005/044766, filed Dec. 8, 2005, mailed Jun. 7, 2006, 10 pgs.

European Search Report for application 05853635.0-2107, mailed Jan. 21, 2008, 3 pgs.

* cited by examiner

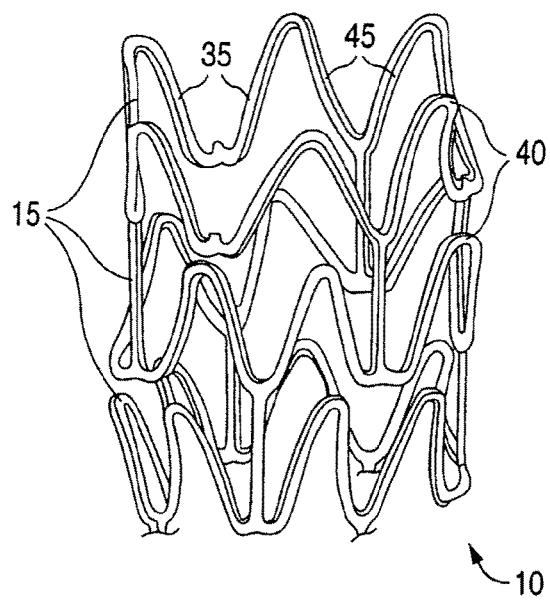
FIG. 1
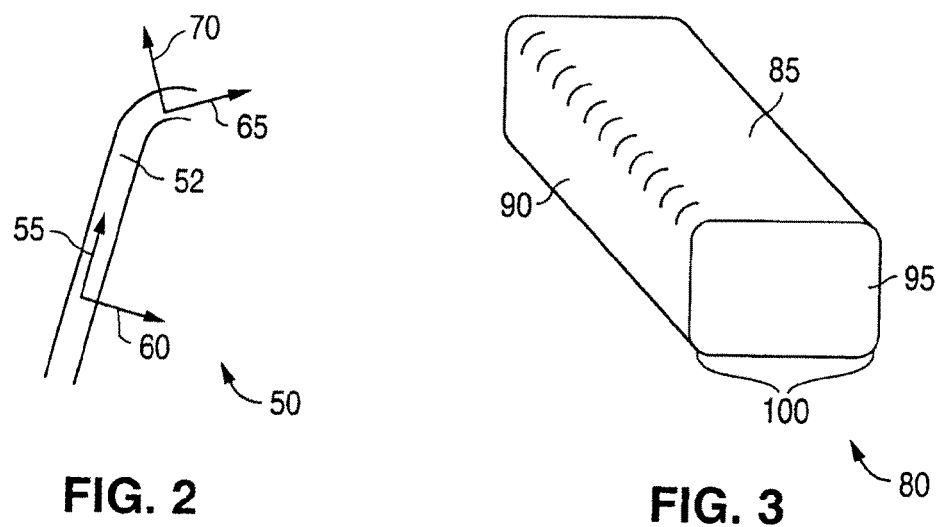
FIG. 2
FIG. 3
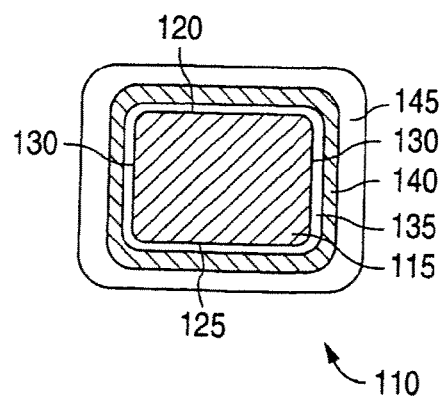
FIG. 4

ABLUMINAL, MULTILAYER COATING CONSTRUCTS FOR DRUG-DELIVERY STENTS

CROSS-REFERENCE TO RELATED APPLICATION

This application is a continuation of application Ser. No. 11/015,313, filed Dec. 16, 2004, now U.S. Pat. No. 7,632,307 which is incorporated herein by reference.

BACKGROUND OF THE INVENTION

1. Field of the Invention

The invention relates to drug delivery implantable medical devices, one example of which is a stent. More particularly, the invention relates to abluminal, multilayer coating constructs for drug-delivery stents.

2. Description of the Background

This invention relates to radially expandable endoprostheses, which are adapted to be implanted in a bodily lumen. An "endoprosthesis" corresponds to an artificial implantable medical device that is placed inside the body. A "lumen" refers to a cavity of a tubular organ such as a blood vessel. A stent is an example of these endoprostheses. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expansion of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

Stents have been made of many materials including metals and polymers. Polymeric materials include both nonbioerodable and bioerodable plastic materials. The cylindrical structure of stents is typically composed of a scaffolding that includes a pattern or network of interconnecting structural elements or struts. The scaffolding can be formed from wires, bars, tubes, or planar films of material rolled into a cylindrical shape. Furthermore, the pattern that makes up the stent allows the stent to be radially expandable and longitudinally flexible. Longitudinal flexibility facilitates delivery of the stent, and rigidity is needed to hold open a body lumen. The pattern should be designed to maintain the longitudinal flexibility and rigidity required of the stent.

Stents are used not only for mechanical intervention but also as vehicles for providing biological therapy. Biological therapy can be achieved by medicating the stents. Medicated stents provide for the local administration of a therapeutic substance at the diseased site. In order to provide an efficacious concentration to the treated site, systemic administration of such medication often produces adverse or even toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

A medicated stent may be fabricated by coating the surface of either a metallic or polymeric scaffolding to produce a drug reservoir layer on the surface. The drug reservoir layer typically includes a polymeric carrier that includes an active agent or drug. To fabricate a coating, a polymer, or a blend of polymers, can be applied on the stent using commonly used techniques known to those having ordinary skill in the art. A composition for application to a stent may include a solvent, a polymer dissolved in the solvent, and an active agent dispersed in the blend. The composition may be applied to the stent by immersing the stent in the composition, by direct application, by roll coating, or by spraying the composition onto the stent. The solvent is allowed to evaporate, leaving on the stent strut surfaces a coating of the polymer and the active agent impregnated in the polymer.

A drug delivery stent coating should meet several well-known criteria including mechanical integrity, controlled release of the drug, and biocompatibility. Active agents within polymer-based coating layers can interfere with the mechanical integrity of a coating since active agents negatively impact the coating mechanical properties, and the ability of a polymer matrix to adhere effectively to the surface of the stent. Increasing the quantity of the active agent reduces the effectiveness of the adhesion. A primer layer can serve as a functionally useful intermediary layer between the surface of the device and an active agent-containing or reservoir coating, or between multiple layers of reservoir coatings. The primer layer provides an adhesive tie between the reservoir coating and the device. In addition, successful treatment of a diseased site with a medicated stent often requires that the rate of release of the active agent or drug be within a prescribed range. A barrier or polymeric topcoat layer above a reservoir layer serves the purpose of controlling the rate of release of an active agent or drug.

Furthermore, since the presence of foreign polymers can adversely affect the body, it is generally desirable to limit exposure of the polymer on a coating to the body. Therefore, a stent may also include a biobeneficial coating over a reservoir layer and/or topcoat layer to improve the biocompatibility of the coating. However, in general, it is appropriate to use no more polymer than is necessary to hold the drug on the stent and to control its release. This is particularly the case for coatings that include bioabsorbable polymers since the polymer is absorbed in vivo. Therefore, it would be advantageous to reduce the amount of coating material on a stent without adversely impacting the stent's treatment capabilities.

Additionally, the presence of a topcoat layer, such as a poly(ester amide) (PEA) layer, on a luminal stent surface can have a detrimental impact on a stent's deliverability and coating mechanical integrity. The PEA coatings change the coefficient of friction between the stent and the delivery balloon. In addition, some PEA polymers have structures that cause them to be sticky or tacky. If the PEA either increases the coefficient of friction or adheres to the catheter balloon, the smooth release of the stent from the balloon after deflation is compromised. PEA stent coatings often exhibit extensive balloon shear damage post-deployment as well, which could result in a thrombogenic luminal stent surface. Therefore, it would be desirable to limit exposure of the balloon to the PEA topcoat layer.

SUMMARY

In some aspects of the invention, an implantable medical devices includes a structural element. A surface of the structural element comprises an abluminal side, a luminal side, a first sidewall, and a second sidewall, the first and second sidewalls extending between the abluminal side and the luminal side, the first sidewall including a first sidewall portion adjacent to the abluminal side. The structural element has a coating comprising a continuous first layer and a continuous second layer. The continuous first layer is disposed above all of the abluminal side and over the first sidewall portion as measured along an axis normal to the first sidewall portion, wherein the luminal side and other portions of the first sidewall are free from the first layer. The continuous second layer covers the first layer such that a portion of the first layer is not covered by the second layer, wherein the luminal side is free from the second layer.

In some aspects of the invention, an implantable medical devices includes a structural element. A surface of the structural element comprises an abluminal side, a luminal side, a first curved surface, a second curved surface, a first sidewall, and a second sidewall, the first and second sidewalls extending between the abluminal side and the luminal side, the first curved surface extending from the first sidewall to the abluminal side, the second curved surface extending from the second sidewall to the abluminal side. The structural element has a coating comprising a continuous first layer and a continuous second layer. The continuous first layer is disposed on a portion of abluminal side, the first layer having a first edge adjacent the first curved surface and a second edge adjacent the second curved surface, wherein the luminal side, the first curved surface, the first and second sidewalls, and other portions of the abluminal side are free from the first layer. The continuous second layer covers the first layer from the first edge of the first layer to the second edge of the first layer, wherein the luminal side, the first curved surface, the first and second sidewalls are free from the second layer.

The features and advantages of the invention will be more readily understood from the following detailed description which should be read in conjunction with the accompanying drawings.

BRIEF DESCRIPTION OF THE FIGURES

FIG. 1 depicts a stent.
FIG. 2 depicts a planar projection of a portion of a stent.
FIG. 3 depicts a portion of a structural element of a stent.
FIG. 4 depicts a cross-section of a structural element of a stent with a coating.

DETAILED DESCRIPTION

Figure 5:
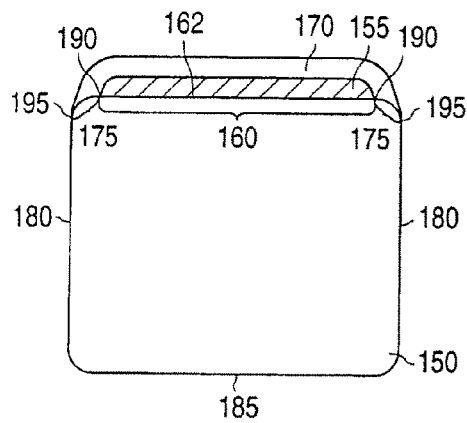
FIG. 5 depicts a cross-sectional view of an embodiment of an abluminally coated structural element of a stent.

Embodiments of the invention described herein relate to drug delivery implantable medical devices. In particular, various embodiments of devices with abluminal, multilayer coating constructs for drug-delivery are described. The embodiments of devices described herein relate to implantable medical devices that include an underlying scaffolding or substrate with a coating such as a polymer-based coating. The polymer-based coating may contain, for example, an active agent or drug for local administration at a diseased site. The active agent can be any substance capable of exerting a therapeutic or prophylactic effect. The underlying substrate that is coated can be polymeric, metallic, ceramic, or made from any suitable material. "Implantable medical device" is intended to include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure or substrate of the device can be of virtually any design.

The underlying structure or substrate of an implantable medical device, such as a stent can be completely or at least in part be made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

To fabricate the coating, the polymer, or a blend of polymers, can be applied on the stent using commonly used techniques known to those having ordinary skill in the art. For example, the polymer can be applied to the stent by dissolving the polymer in a coating solvent, or a mixture of solvents, and applying the resulting solution on the stent by spraying, "ink-jet-type" deposition methods, brushing, roll coating, plasma deposition, and the like. "Solvent" is defined as a substance capable of dissolving or dispersing one or more other substances or capable of at least partially dissolving or dispersing the substance(s) to form a uniformly dispersed mixture at the molecular- or ionic-size level. The solvent should be capable of dissolving at least 0.1 mg of the polymer in 1 ml of the solvent, and more narrowly 0.5 mg in 1 ml at ambient temperature and ambient pressure.

Polymers can be biostable, bioabsorbable, biodegradable, or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like. For coating applications, it is understood that after the process of degradation, erosion, absorption, and/or resorption has been completed, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used in the embodiments of the substrate of implantable medical devices or coatings for implantable medical devices disclosed herein include, but are not limited to, poly(N-acetylglucosamine) (Chitin), Chitosan, poly(hydroxyvalerate), poly (lactide-co-glycolide), poly(hydroxybutyrate), poly(hydroxybutyrate-co-valerate), polyorthoester, polyanhydride, poly(glycolic acid), poly(glycolide), poly(L-lactic acid), poly (L-lactide), poly(D,L-lactic acid), poly(D,L-lactide), poly (D-lactic acid), poly(D-lactide), poly(D,L-lactide-co-L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), poly(methacrylates), poly(acrylates), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in embodiments of the substrate of implantable medical devices or coatings for implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

In addition, polymers containing moieties derived from poly(lactic acid) can be also used in addition to or instead of, poly(lactic acid), for fabricating and coating devices. Polymers based on poly(lactic acid) include derivatives of poly (lactic acid), for example, hydrolyzed or carboxylated poly (lactic acid), or a blend thereof. Using hydrolyzed or carboxylated poly(lactic acid) is expected to result in an increased rate of degradation of the coating. Another type of polymer based on poly(lactic acid) that can be used for fabricating and coating implantable medical devices includes graft copolymers, and block copolymers, such as AB block-copolymers ("diblock-copolymers") or ABA block-copolymers ("triblock-copolymers"), or mixtures thereof.

Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2',6,6'-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, and 40-O-tetrazole-rapamycin.

A non-polymer substrate of the device may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Embodiments of the devices described herein may be illustrated by a stent. FIG. 1 depicts an example of a three-dimensional view of a stent 10. The stent may be made up of a pattern of a number of interconnecting structural elements or struts 15. The embodiments disclosed herein are not limited to stents or to the stent pattern illustrated in FIG. 1. The embodiments are easily applicable to other patterns and other devices. The variations in the structure of patterns are virtually unlimited.

Additionally, a surface of an implantable medical device may also be characterized by the relative location of the surface with respect to a bodily lumen. The device may include luminal surfaces or inner portions, abluminal surfaces or outer portions, and surfaces between the luminal and abluminal surfaces or side-wall surfaces. For example, struts 15 of stent 10 include luminal surfaces 35, abluminal surfaces 40, and side-wall surfaces 45. A strut may also be described by axes, a longitudinal axis and a latitudinal axis. FIG. 2 depicts a planar projection of an abluminal or luminal surface 52 of a portion 50 of a strut depicting a longitudinal axis 55 and a latitudinal axis 60 along a straight section of portion 50. A longitudinal axis 65 on a curved section of a strut may be defined as a tangent to a curvature at a location on the curved section. A corresponding latitudinal axis 70 is perpendicular to longitudinal axis 65.

FIG. 3 depicts a three-dimensional cut-out portion 80 of a structural element or strut from a stent. Portion 80 illustrates an abluminal surface 85 and a side-wall surface 90. The luminal surface and an opposing side-wall surface are hidden. A cross-section 95 of portion 80 is rectangular with rounded corners 100. Portion 80 is shown only for the purpose of illustrating the embodiments described herein. The embodiments are not limited to the particular geometry of portion 80 and are easily applicable to other strut geometries. The cross-section of a structural element may have sharp corners that sharply delineate an edge or boundary between abluminal/luminal surfaces and side-wall surfaces. In addition, virtually any cross-sectional shape is applicable, for example, circular, square, elliptical, trapezoidal, etc.

As indicated above, a drug delivery coating for a stent with a structural element like that depicted in FIG. 3 may be designed to meet several criteria including mechanical integrity (e.g., adhesion), controlled release of the drug, and biocompatibility. Coating configurations designed to meet these criteria can include any number and combination of layers. In some embodiments, the coatings may include one or a combination of the following four types of layers:

(a) a primer layer, which may improve adhesion of subsequent layers on the implantable substrate or on a previously formed layer;

(b) a reservoir or agent layer, which may include a polymer and an agent or, alternatively, a polymer free agent;

(c) a topcoat layer, which may serve as a way of controlling the rate of release of an agent from a reservoir layer; and (d) a biobeneficial or biocompatible finishing layer containing a biobeneficial agent, which may improve the biocompatibility of the coating.

The reservoir layer can be applied directly to at least a part of a surface of an implantable medical device as a pure agent to serve as a reservoir for at least one active agent. The agent can be combined with a biodegradable polymer as a matrix, wherein the agent may or may not be bonded to the polymer. The primer layer can be applied between the surface of the device and the agent layer to improve adhesion of the agent layer to the surface or between layers and can optionally include an agent. A layer of pure or substantially pure active agent can be sandwiched between layers including biodegradable polymer. For example, it has been observed that a reservoir layer containing principally EVEROLIMUS has very poor adhesion to metallic struts. A primer layer, including, for example, poly(butyl methacrylate) (PBMA) enables an EVEROLIMUS reservoir layer to remain on the stent. The topcoat layer can be applied over at least a portion of the reservoir layer to serve as a membrane to control the rate of release of the active agent and can optionally comprise an agent.

The biobeneficial finishing layer can also be applied to increase the biocompatibility of the coating by, for example, increasing acute hemocompatibility and can also include an active agent. A "biobeneficial agent" is an agent linked to a polymer that provides a biological benefit within a mammal without necessarily being released from the polymer. A biological benefit may be that the polymer or coating is modified with the biobeneficial agent to be non-thrombogenic, such that protein absorption is inhibited or prevented to avoid formation of a thromboembolism; to promote healing, such that endothelialization of the luminal stent surfaces is rapid and forms a healthy and functional endothelial layer; or to be non-inflammatory, such that the biobeneficial agent acts as a biomimic to passively avoid attracting monocytes and neutrophils, which leads to the cascade of events creating inflammation. The biobeneficial agent can also be combined, mixed or blended with a polymer. Representative examples of biobeneficial agents include, but are not limited to, poly(alkylene glycols), poly(N-vinyl pyrrolidone), poly(acrylamide methyl propane sulfonic acid), poly(styrene sulfonate), sulfonated dextran, polyphosphazenes, poly(orthoesters), poly (tyrosine carbonate), hyaluronic acid, heparin and any derivatives, hirudin, analogs, homologues, congeners, salts, copolymers and combinations thereof.

Coating configurations on stents with one or more of the above types of layers are typically conformal, which is a coating that covers all or most of the surfaces of the struts, including the abluminal surface, luminal surface, and side-wall surfaces. FIG. 4 illustrates an exemplary conformal drug delivery coating. A cross-section 110 of a strut 115 from a stent is depicted in FIG. 4. Strut 115 has a multilayer coating on all four of its surfaces, an abluminal surface 120, luminal surface 125, and both side surfaces 130. The multilayer coating has an innermost primer layer 135 below a reservoir layer 140. A topmost layer is a topcoat layer 145 for controlling the release of active agent or drug from reservoir layer 140. Active agent may also be incorporated into topcoat layer 145 to modulate the initial release rate of active agent or to reduce sticking of the topcoat layer to a catheter balloon during delivery and deployment of a stent.

It would be desirable to have a drug delivery coating restricted completely or substantially to an abluminal surface of a stent that also addresses one or more of the criteria discussed above including mechanical integrity, controlled release, and biocompatibility. There are several advantages of having a drug delivery coating restricted completely to an abluminal surface region of a strut. From a therapeutic standpoint, an abluminal coating can be as efficacious as a conformal coating. Furthermore, an abluminal coating allows a reduction in the total polymer load on a stent, which may improve the biocompatibility of the stent. A lower polymer loading reduces the form factor of the stent which reduces the disturbance of the local blood flow, and hence, the thrombogenecity of the stent. Additionally, a decreased polymer load for biodegradable coatings reduces the likelihood of embolization due to particles of degrading polymer in the blood stream.

Another advantage of a coating restricted completely or substantially to the abluminal surface is that interactions between a topcoat layer and the catheter balloon are reduced or eliminated. It has been observed that use of an outermost topcoat layer, in particular poly(ester amide), on a luminal stent surface can have a detrimental impact on a stent's deliverability and coating mechanical integrity. The PEA coating changes the coefficient of friction between the stent and the delivery balloon. Additionally, some PEA polymers have structures that cause them to be sticky or tacky. If the PEA either increases the coefficient of friction or adheres to the catheter balloon, the smooth release of the stent from the balloon after deflation is compromised. PEA stent coatings have been observed to exhibit extensive balloon shear damage post-deployment as well, which could increase the thrombogenicity of the luminal stent surface.

The abluminal, multilayer coating configurations described herein possess the advantages discussed above and meet one or more of the criteria of mechanical integrity, controlled release, and biocompatibility. Additionally, the coatings allow controlled release from an abluminal reservoir layer without the use of reservoirs embedded in cavities or indentations in the abluminal surface. The surfaces of the structural members of the implantable medical devices used for conformal coatings are identical to those used in the presently described abluminal coating embodiments.

Embodiments of polymer coatings are illustrated by FIGS. 5-15A-B. The figures have not been drawn to scale, and the thickness of the various layers have been over or under emphasized for illustrative purposes. The polymers used for the primer material should have a high capacity of adherence to the surface of an implantable device, such as a metallic surface of a stent, or a high capacity of adherence to a polymeric surface such as the surface of a stent made of polymer, or a previously applied layer of polymeric material. The polymer in primer layers may be a homopolymer, copolymer, terpolymer, etc. The polymer may also include random, alternating, block, cross-linked, blends, and graft variations thereof. For instance, a primer layer may include PEA, poly(butyl methacrylate), or a poly(lactic acid). The active agent may be, for example, 40-O-(2-hydroxy)ethyl-rapamycin, known by the trade name of EVEROLIMUS, available from Novartis as Certican™. The active agent may be dispersed in a polymer such as poly(vinylidene fluoride-co-hexafluoropropene) (Solef). A topcoat or barrier layer may be any polymer that controls the migration of active agent. For example, the topcoat layer may include PEA.

By way of example, and not limitation, a primer layer can have any suitable thickness, examples of which can be in the range of about 0.1 to about 10 microns, or more narrowly about 0.1 to about 2 microns. A reservoir layer can have a thickness of about 0.1 microns to about 20 microns, or more narrowly about 0.5 microns to 15 microns. The amount of the active agent to be included on an implantable medical device can be further increased by applying a plurality of reservoir layers on top of one another. A topcoat layer can have any suitable thickness, examples of which can be in the range of about 0.1 to about 20 microns, or more narrowly about 0.1 to about 10 microns.

"Above" a surface or layer is defined as higher than or over a surface or layer measured along an axis normal to a surface, but not necessarily in contact with the surface or layer. "Below" is defined as the opposite of "above." "Cover" is defined as above and in contact with. "Continuous" is defined as marked by uninterrupted extension in space. As used herein, an "edge" of a layer refers to a line or region on a surface delineating where the layer ends.

A structural element of an implantable medical device, such as a stent, suitable for coating embodiments disclosed herein may include a surface having an abluminal side, a luminal side, and two sidewalls extending between the abluminal side and the luminal side. Several embodiments include coating layers above the abluminal side, and optionally over a minor portion of one or both of the sidewalls adjacent to the abluminal side. Some of these abluminal or substantially abluminal coating embodiments include controlled release of active agents from a reservoir layer and/or improved adhesion due to primer layer(s). In the embodiments of the coatings described below, the surface of the structural element below the coating is cavity free.

One embodiment of a coating on a structural element of an implantable medical device may include a continuous first layer disposed above a majority of the abluminal side. The continuous first layer may optionally be above a portion of at least one of the side-walls extending from the abluminal side. The luminal side and portions of the sidewalls may be free from the first layer.

The coating may further include a continuous second layer covering the first layer such that no portion of the first layer is not covered by the second layer. The luminal side of the structural element may be free from the second layer. In some embodiments, the second layer may cover a portion of the structural element not covered by the first layer. In one embodiment of the coating, a majority of the sidewalls may be free from the first layer and the second layer.

It may be advantageous to have a third layer above the reservoir layer that may function as a topcoat layer, primer layer, and/or biobeneficial layer. A topcoat layer may control the release of active agent from the reservoir layer. Additionally, a third layer functioning as a primer layer may improve the adhesion between a second layer and another layer above the second layer. In some embodiments, a continuous third layer may cover the second layer such that no portion of the second layer is not covered by the third layer. Additionally, the third layer may cover a portion of the structural element not covered by the second layer.

In one embodiment, a majority of the sidewalls may be free from the third layer. Alternatively, the third layer may cover a portion of or all of the sidewalls.

In a further embodiment, the luminal side of the structural element may be free from the third layer. Alternatively, the third layer may cover a portion of or the entire luminal side.

In certain embodiments, at least one of the first or second layers may be a reservoir layer that includes a pure or substantially pure active agent. In one such embodiment, the first layer may be a reservoir layer. In this embodiment, the second layer may be a topcoat or barrier layer that functions to control the release of active agent from the reservoir layer. The second layer may additionally or alternatively function as a primer layer that improves adhesion between the reservoir layer and another layer above the second layer.

FIG. 5 is a cross-sectional view of an embodiment of an abluminally coated structural element 150. Structural element 150 has a coating with a reservoir layer 155 above a portion 160 of an abluminal surface 162. The coating also includes a second layer 170 above reservoir layer 155 and two additional portions 175 of the surface not below first layer 155. Additional portions 175 are adjacent to edges 190 of reservoir layer 155. Furthermore, additional portions 175 include a portion of abluminal surface 162 and sidewall surfaces 180 since edges 195 of second layer 170 lie on side-wall surfaces 180. A majority of the sidewall surfaces 180 and all of a luminal surface 185 are free of reservoir layer 155 and second layer 170. As indicated above, second layer 170 may be a topcoat or barrier layer. In this case, the topcoat layer effectively seals in the reservoir layer and controls the release rate of an active agent from reservoir layer 155.

Figure 6:
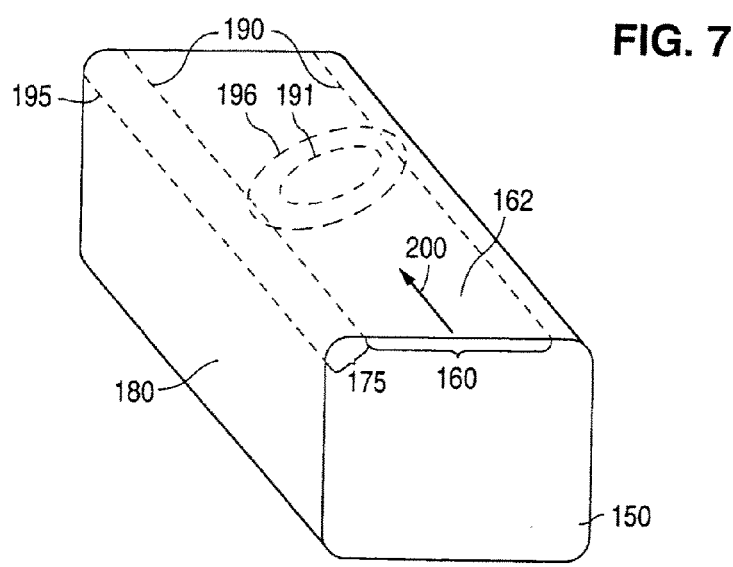
FIG. 6 depicts a three-dimensional view showing the edges of coating layers illustrated in FIG. 5.

In certain embodiments, coating layers in an abluminal or substantially abluminal coating may be strip-shaped with at least one edge of a coating layer parallel to a longitudinal axis of the structural element. As an illustration, FIG. 6 depicts a three-dimensional rendering of a portion of structural element 150 illustrating embodiments of coating layers of the coating shown in FIG. 5. FIG. 6 illustrates a strip-shaped reservoir layer 155 and strip-shaped second layer by showing the outline of edges 190 of reservoir layer 155 and edges 195 of second layer 170. Edges 190 and 195 are parallel to a longitudinal axis 200 of structural member 150. In other embodiments, an abluminal or substantially abluminal coating may have any useful shape, for example, disc-shaped, rectangular, etc. FIG. 6 also depicts reservoir layer 155 and second layer 170 as disc-shaped with edges 191 and 196, respectively.

Figure 7:
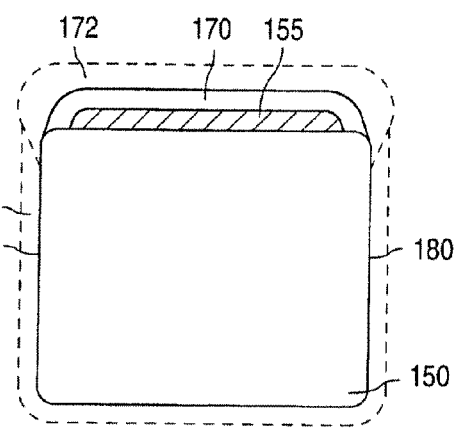
FIG. 7 depicts the coating embodiment in FIG. 5 with a biobeneficial layer.

FIG. 7 illustrates the use of a biobeneficial layer with the coating configuration from FIG. 5. In FIG. 7, a biobeneficial layer 172 is shown covering all of second layer 170 and a portion of sidewall 180. An alternative biobeneficial layer 173 is also shown that covers all of second layer 170 and the remaining portion of the surface of the structural member 150.

In alternate embodiment, the second layer may be a reservoir layer. In this embodiment, the first layer may then be primer layer that improves adhesion between a reservoir layer and a surface or another layer.

Figure 8:
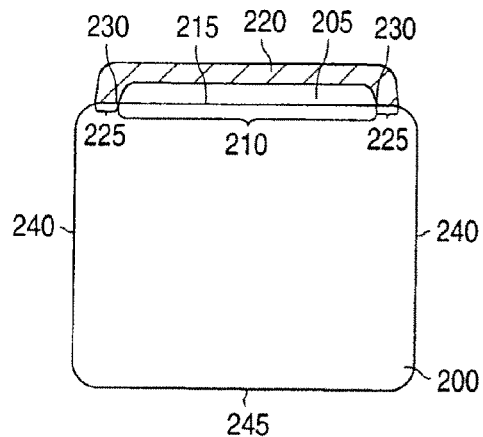
FIG. 8 depicts a cross-sectional view of an embodiment of an abluminally coated structural element of a stent.

FIG. 8 is a cross-sectional view of an embodiment of a structural member 200 having a coating with a primer layer 205 above a portion 210 of an abluminal surface 215. The coating also includes a reservoir layer 220 above primer layer 205 and two additional portions 225 of the surface not below primer layer 205. Additional portions 225 are adjacent to edges 230 of primer layer 205. All of the side-wall surfaces 240 and a luminal surface 245 are not below primer layer 205 and reservoir layer 220.

Figure 9:
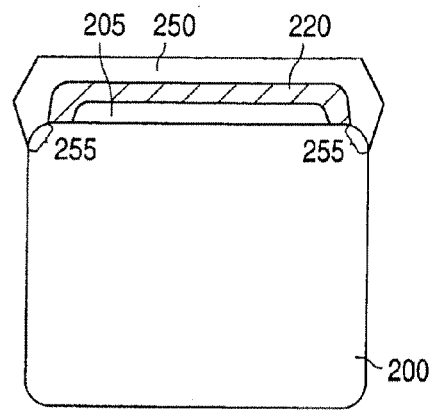
FIG. 9 depicts the coating embodiment illustrated in FIG. 8 with a third layer.

As discussed above, it may be advantageous to have third layer above the reservoir layer that functions as a topcoat and/or biobeneficial layer. FIG. 9 depicts the coating illustrated in FIG. 8 with a third layer 250 above reservoir layer 220. Third layer 250 covers reservoir layer 220 and portions 255 of the surface of structural member 200. The structural member may further include a fourth layer, for example, a biobeneficial layer covering the third layer and a portion or the entire surface not below the other third layer.

Other embodiments of a coating on a structural element may include a continuous first layer disposed above a majority of the abluminal side of the structural element and optionally above a portion of at least one of the side-walls extending from the abluminal side. The luminal side and portions of the sidewalls may be free from the first layer. The coating may also include a continuous second layer covering a portion of the first layer such that at least a portion of the first layer is not covered by the second layer. A majority of the sidewalls may be free from the first layer and the second layer. In an embodiment, the second layer may be a reservoir layer and the first layer may be a primer layer that improves adhesion of the reservoir layer to the surface of the structural element.

Figure 10:
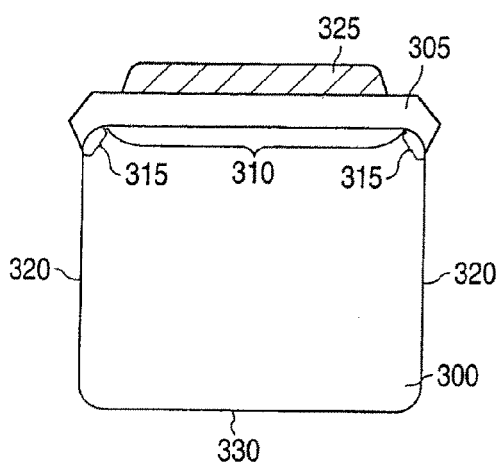
FIG. 10 depicts a cross-sectional view of an embodiment of an abluminally coated structural element of a stent.

FIG. 10 is a cross-sectional view of an embodiment of a coated structural element 300. Structural element 300 has a coating with a primer layer 305 above an abluminal surface 310 and portions 315 of sidewall surfaces 320. The coating also includes a reservoir layer 325 above a portion of primer layer 305. Most of the side-wall surfaces 320 and the entire luminal surface 330 are free of the primer layer 305 and reservoir layer 325.

Additionally, an embodiment exemplified in FIG. 10 may further include a third layer above the reservoir layer, which may function as a topcoat layer, primer layer, and/or biobeneficial layer. The third layer may be a continuous layer covering the second layer such that no portion of the second layer is not covered by the third layer. In some embodiments, a third layer may be above a portion, but not the entire first layer. Alternatively, the third layer may be above the entire first layer. In addition, the third layer may cover the entire first layer and a portion of the surface of the structural element not covered by the first layer. In one embodiment, a majority of the sidewalls may be free from the third layer.

Figure 11:
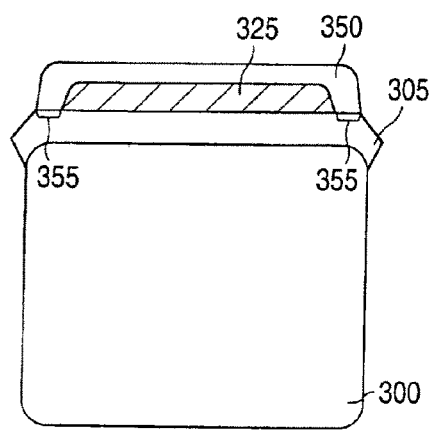
FIG. 11 depicts the coating embodiment illustrated in FIG. 10 with a third layer.

FIG. 11 depicts the coating illustrated in FIG. 10 with a third layer 350 above reservoir layer 325. Third layer 350 covers reservoir layer 325 and portions 355 of primer layer 305.

The structural member may further include a fourth layer covering the third layer such that no portion of the third layer is not covered by the fourth layer. The fourth layer may be a biobeneficial coating layer that increases biocompatibility of the coating.

Furthermore, numerous variations of the coating embodiments described above are possible. Such variations may be configured to achieve release control of active agent from a reservoir layer, improve adhesion between layers, and/or improve biocompatibility of the coating. In certain embodiments, abluminal or substantially abluminal coating embodiments may have multiple primer and reservoir layers with the layers alternating between the two types of layers through the thickness of the coating. Such embodiments may be useful, for example, for a course of treatment that occurs in stages where each stage requires the use of a different type or types of active agents.

Moreover, multiple primer and reservoir embodiments may utilize the release control topcoat-reservoir embodiment exemplified in FIG. 5 and the adhesion improvement primer-reservoir embodiments exemplified in FIGS. 8 and 10. FIG. 8 exemplifies an embodiment in which a reservoir layer is above a portion of the primer layer and a portion of the surface not below the primer layer. FIG. 10 exemplifies an embodiment in which a reservoir layer is above a portion of the primer layer.

Figure 12:
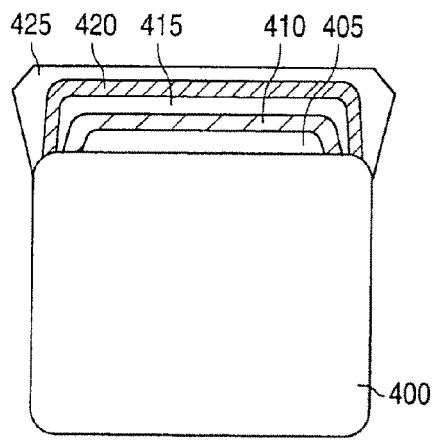
FIG. 12 depicts a multiple primer and reservoir layer coating with repeat units of the embodiment exemplified in FIG. 8.

One embodiment of a multiple primer and reservoir layer coating may include repeat units of the embodiment exemplified in FIG. 8. FIG. 12 illustrates such a multilayer embodiment. FIG. 12 depicts structural element 400 with a first primer layer 405, a first reservoir layer 410, a second primer layer 415, and a second reservoir layer 420. A topcoat layer 425, for controlling the release of active agent from first reservoir layer 410 and second reservoir layer 420, is also shown. Second primer layer 415 may also act to control the release of active agent form first reservoir layer 410. The combination of second reservoir layer 420 and topcoat layer 425 utilizes the embodiment exemplified in FIG. 5.

Figure 13:
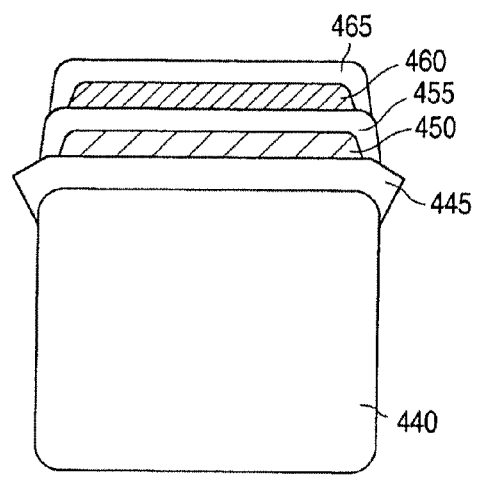
FIG. 13 depicts a multiple primer and reservoir layer coating with repeat units of the embodiment exemplified in FIG. 10.

Another embodiment of a multiple primer and reservoir layer coating may include repeat units of the embodiment exemplified in FIG. 10. FIG. 13 illustrates such an embodiment. FIG. 13 depicts structural element 440 with a first primer layer 445, a first reservoir layer 450, a second primer layer 455, and a second reservoir layer 460. A topcoat layer 465, for controlling the release of active agent from first reservoir layer 450 and second reservoir layer 460, is also shown. Second primer layer 455 may also act to control the release of active agent from first reservoir layer 450.

Figure 14A:
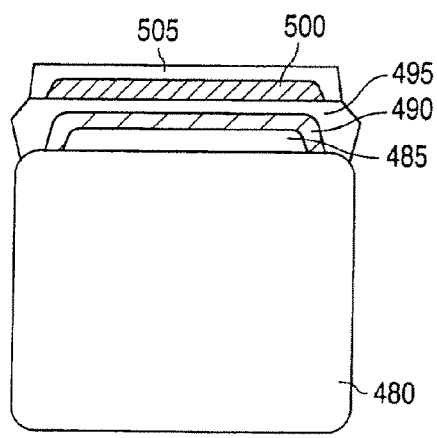
FIG. 14A depicts a multiple primer and reservoir layer coating with the embodiment exemplified in FIG. 8 below the embodiment exemplified in FIG. 10.

A further embodiment of a multiple primer and reservoir layer coating may include the embodiment exemplified in FIG. 8 below the embodiment exemplified in FIG. 10. FIG. 14A depicts structural element 480 with a first primer layer 485, a first reservoir layer 490, a second primer layer 495, and a second reservoir layer 500. A topcoat layer 505, for controlling the release of active agent from first reservoir layer 490 and second reservoir layer 500, is also shown. Second primer layer 495 may also act to control the release of active agent from first reservoir layer 490.

Figure 14B:
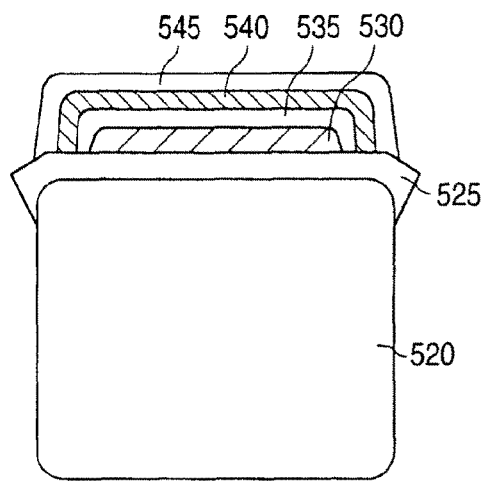
FIG. 14B depicts a multiple primer and reservoir layer coating with the embodiment exemplified in FIG. 10 below the embodiment exemplified in FIG. 8.

Additionally, the embodiment exemplified in FIG. 10 may be below the embodiment exemplified in FIG. 8. FIG. 14B depicts structural element 520 with a first primer layer 525, a first reservoir layer 530, a second primer layer 535, and a second reservoir layer 540. A topcoat layer 545, for controlling the release of active agent from first reservoir layer 530 and second reservoir layer 540, is also shown. Second primer layer 535 may also act to control the release of active agent from first reservoir layer 530.

Figure 15A:
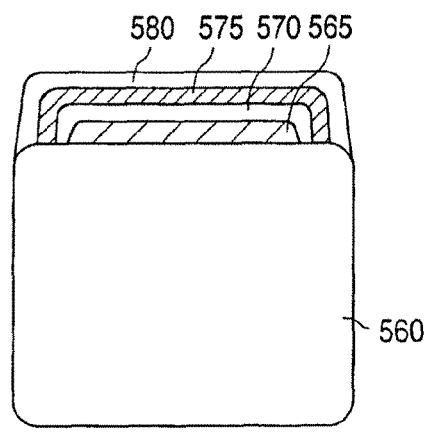
FIG. 15A depicts a coating that includes the coating of FIG. 5 below the embodiment exemplified by FIG. 8.

In addition, a multiple primer and reservoir coating may include the coating shown in FIG. 5, with topcoat layer 170 acting as a primer layer, combined with the embodiments exemplified by FIG. 8 and/or FIG. 10. FIG. 15A illustrates a coating that includes the coating of FIG. 5 below the embodiment exemplified by FIG. 8. FIG. 15A depicts structural element 560 with a first reservoir layer 565, a first primer layer 570, and a second reservoir layer 575. A topcoat layer 580, for controlling the release of active agent from first reservoir layer 565 and second reservoir layer 575, is also shown.

Figure 15B:
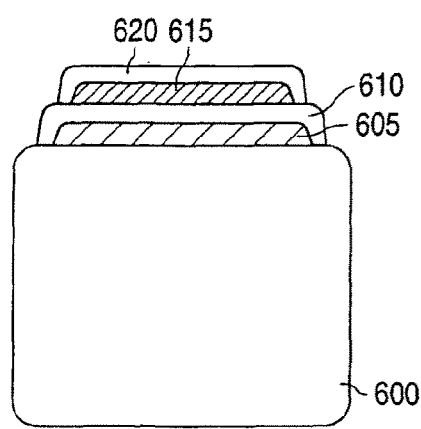
FIG. 15B depicts a coating that includes the coating of FIG. 5 below the embodiment exemplified by FIG. 10.

Additionally, FIG. 15B illustrates a coating that includes the coating of FIG. 5 below the embodiment exemplified by FIG. 10. FIG. 15B depicts structural element 600 with a first reservoir layer 605, a first primer layer 610, and a second reservoir layer 615. A topcoat layer 620, for controlling the release of active agent from first reservoir layer 605 and second reservoir layer 615, is also shown.

Various methods may be used to form coatings as described herein including, but not limited to, ink-jet-type coating, electrostatic coating, roll coating, thermal deposition with masking, plasma polymerization with masking, direct application of polymer/solvent solution by micro-syringe, direct polymer melt application, and spray coating with photomasking. For example, a controlled deposition system ink-jet-type coating method can be used that applies various substances only to certain targeted portions of an implantable medical device. A representative example of such a system, and a method of using the same, is described in U.S. Pat. No. 6,395,326 to Castro et al. A controlled deposition system can be capable of depositing a substance on an implantable medical device having a complex geometry, and otherwise apply the substance so that coating is limited to particular portions of the device. The system can have a dispenser and a holder that supports the medical substrate. The dispenser and/or holder can be capable of moving in very small intervals, for example, less than about 0.001 inch. Furthermore, the dispenser and/or holder can be capable of moving in the x-, y-, or z-direction, and be capable of rotating about a single point.

The controlled deposition system can include a dispenser assembly. The dispenser assembly can be a simple device including a reservoir, which holds a composition prior to delivery, and a nozzle having an orifice through which the composition is delivered. One exemplary type of dispenser assembly can be an assembly that includes an ink-jet-type printhead. Another exemplary type of a dispenser assembly can be a microinjector capable of injecting small volumes ranging from about 2 to about 70 nL, such as NanoLiter 2000 available from World Precision Instruments or Pneumatic PicoPumps PV830 with Micropipette available from Cell Technology System. Such microinjection syringes may be employed in conjunction with a microscope of suitable design.

Furthermore, selective coating of an implantable medical device may be performed using photomasking techniques. Deposition and removal of a mask can be used to selectively coat surfaces of substrates. Masking deposition is known to one having ordinary skill in the art.

Additionally, the substances of the present invention can also be selectively deposited by an electrostatic deposition process. Such a process can produce an electrically charged or ionized coating substance. The electric charge causes the coating substance to be differentially attracted to the device, thereby resulting in higher transfer efficiency. The electrically charged coating substance can be deposited onto selected regions of the device by causing different regions of the device to have different electrical potentials.

FIGS. 16-20 illustrate examples of the use of electrostatic coating to coat a stent. FIGS. 16-20 depict scanning electron micrograph (SEM) images of stents with poly(ester amide) (PEA) coatings. The stent used in the examples is a metallic Vision stent obtained from Guidant Corporation in Santa Clara, Calif. The stents had a 3 mm outside diameter and were 12 mm in length.

Figure 16:
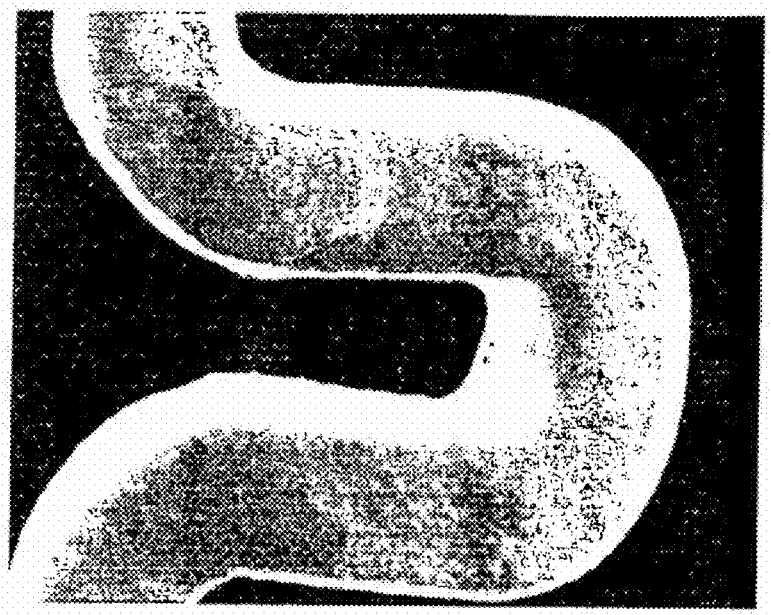
FIG. 16 depicts an SEM image of an abluminal surface of an electrostatically coated stent after wet expansion.
Figure 17:
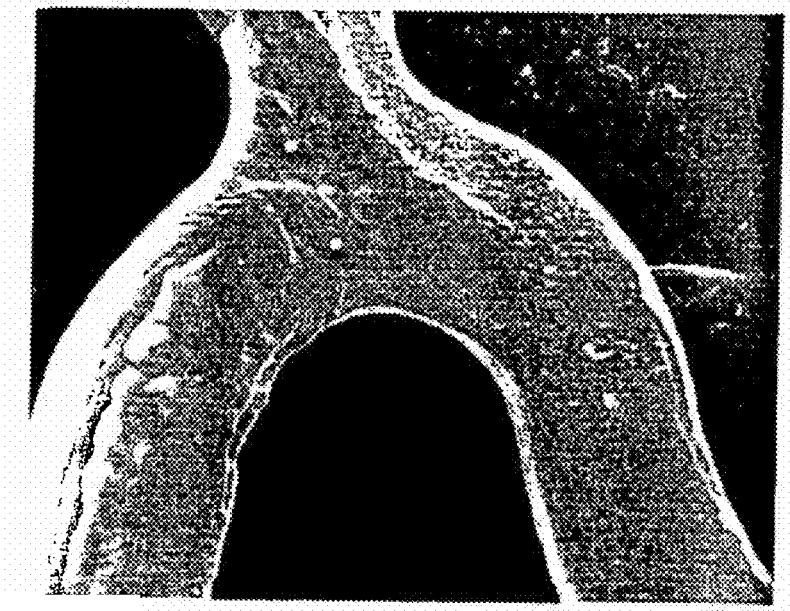
FIG. 17 depicts an SEM image of a luminal surface of an electrostatically coated stent after wet expansion.
Figure 18:
FIG. 18 depicts an SEM image of a luminal surface of an electrostatically coated stent after wet expansion.

An electrostatic coating method was used to coat the stent with a total solid of 328 μg using a 2% by weight solution of PEA-TEMPO in ethanol. PEA-TEMPO may be obtained from Guidant Corporation. The stent was translated and rotated under an electrospray nozzle. A different electrical potential on the luminal and abluminal surfaces was created by using a plastic sleeve over a spray mandrel. The plastic sleeve repelled the same charged droplets which prevented the droplets from depositing onto the luminal side of the stent. This resulted in a thinner coating layer on the luminal surface than the abluminal surface. A syringe pump was controlled at 1 cc/hr, and voltage was set at 5 kV. The coated stent was oven dried at 50° C. for 30 minutes. FIG. 16 depicts an SEM image of an abluminal surface of the stent after wet expansion of the stent using a catheter balloon with an outside diameter of 3.5 mm. The coating is intact, as shown by the image. FIGS. 17 and 18 depict the luminal surfaces of the stent after the wet expansion. The thin layer of coating in FIGS. 17 and 18 exhibits minor to moderate balloon shear damage.

Figure 19:
FIG. 19 depicts an SEM image of a luminal surface of a conventionally coated stent after dry expansion.
Figure 20:
FIG. 20 depicts an SEM image of a luminal surface of a conventionally coated stent after wet expansion.

Another of the same type of stent was coated using conventional spray coating to compare with the electrostatically coated stent. The stent was coated with 300 μg of 2% by weight solution of PEA-TEMPO in ethanol. The coated stent was oven dried at 50° C. for 30 minutes. FIG. 19 depicts a luminal surface after dry expansion with a catheter balloon of the conventionally coated stent to an outside diameter of 3.33 mm. FIG. 19 shows a thicker coating than what is obtained using electrostatic coating (see FIGS. 17 and 18). FIG. 20 shows the luminal surface of the conventionally coated stent after wet expansion with a catheter balloon with an outside diameter of 3.3 mm. FIG. 20 shows extensive balloon shear damage to the thicker PEA-TEMPO coating. The damage to the coating was much more extensive than the electrostatically applied coating (see FIGS. 17 and 18).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A structural element of an implantable medical device, a surface of the structural element comprises an abluminal side, a luminal side, a first sidewall, and a second sidewall, the first and second sidewalls extending between the abluminal side and the luminal side, the first sidewall including a first sidewall portion adjacent to the abluminal side, wherein the structural element has a coating comprising:
   a continuous first layer disposed above all of the abluminal side and over the first sidewall portion as measured along an axis normal to the first sidewall portion, wherein the luminal side and other portions of the first sidewall are free from the first layer; and
   a continuous second layer covering the first layer such that a portion of the first layer is not covered by the second layer, wherein the luminal side is free from the second layer.

2. The structural element of claim 1, wherein a majority of the first sidewall and a majority of the second sidewall are free from the first layer.

3. The structural element of claim 2, wherein the first sidewall and the second sidewall are free from the second layer.

4. The structural element of claim 2, wherein second layer covers no portion of the structural element not covered by the first layer.

5. The structural element of claim 1, wherein the portion of the first layer not covered by the second layer includes a first edge of the first layer, the first edge located over the first sidewall portion as measured along an axis normal to the first sidewall portion.

6. The structural element of claim 1, wherein the second sidewall includes a second sidewall portion adjacent to the abluminal side, and the first layer is located over the second sidewall portion as measured along an axis normal to the second sidewall portion.

7. The structural element of claim 6, wherein the portion of the first layer not covered by the second layer includes a first edge of the first layer and a second edge of the first layer, the first edge located over the first sidewall portion as measured along an axis normal to the first sidewall portion, the second edge located over the second sidewall portion as measured along an axis normal to the second sidewall portion.

8. The structural element of claim 1, wherein the coating further comprises a continuous third layer covering the second layer such that no portion of the second layer is not covered by the third layer.

9. The structural element of claim 8, wherein a majority of the first sidewall and a majority of the second sidewall are free from the first layer.

10. The structural element of claim 9, wherein second layer and the third layer cover no portion of the structural element not covered by the first layer.

11. The structural element of claim 8, wherein a first edge of the first layer is not covered by the second layer and the third layer, the first edge located over the first sidewall portion as measured along an axis normal to the first sidewall portion.

12. The structural element of claim 11, wherein the second sidewall includes a second sidewall portion adjacent to the abluminal side, the first layer is located over the second sidewall portion as measured along an axis normal to the second sidewall portion, and wherein a second edge of the first layer is not covered by the second layer and the third layer, the second edge located over the second sidewall portion as measured along an axis normal to the second sidewall portion.

13. The structural element of claim 1, wherein the structural element comprises a material selected from the group consisting of a biodegradable polymer, poly(ester amide), and metal.

14. The structural element of claim 1, wherein the implantable medical device is a stent.

15. The structural element of claim 1, wherein the structural element includes no cavity below the coating.

16. The structural element of claim 1, wherein at least one of the first layer and the second layer is a reservoir layer comprising 40-O-(2-hydroxy)ethyl-rapamycin, 40-O-(3-hydroxy)propyl-rapamycin, 40-O-[2-(2-hydroxy)ethoxy]ethyl-rapamycin, and/or 40-O-tetrazole-rapamycin.

17. The structural element of claim 1, wherein at least one of the first layer and the second layer is a reservoir layer comprising a pure or substantially pure active agent.

18. A structural element of an implantable medical device, a surface of the structural element comprises an abluminal side, a luminal side, a first curved surface, a second curved surface, a first sidewall, and a second sidewall, the first and second sidewalls extending between the abluminal side and the luminal side, the first curved surface extending from the first sidewall to the abluminal side, the second curved surface extending from the second sidewall to the abluminal side, wherein the structural element has a coating comprising:
   a continuous first layer disposed on a portion of abluminal side, the first layer having a first edge adjacent the first curved surface and a second edge adjacent the second curved surface, wherein the luminal side, the first curved surface, the first and second sidewalls, and other portions of the abluminal side are free from the first layer; and
   a continuous second layer covering the first layer from the first edge of the first layer to the second edge of the first layer, wherein the luminal side, the first curved surface, the first and second sidewalls are free from the second layer.

19. The structural element of claim 18, wherein the second curved surface is free from the first layer and the second layer.

20. The structural element of claim 18, wherein the second layer has a first edge adjacent the first curved surface and a second edge adjacent the second curved surface, and the coating further comprises a continuous third layer covering the second layer from the first edge of the second layer to the second edge of the second layer,
   the third layer extending from the first edge of the second layer to the second edge of the second layer.

21. The structural element of claim 20, wherein a first edge of the third layer is on the first curved surface, and a second edge of the third layer is on the second curved surface.

* * * * *